United States Patent
Gamcsik et al.

(10) Patent No.: US 6,825,206 B1
(45) Date of Patent: Nov. 30, 2004

(54) CAMPTOTHECIN COMPOUNDS WITH A THIOETHER GROUP

(75) Inventors: Michael P. Gamcsik, Chapel Hill, NC (US); David J. Adams, Chapel Hill, NC (US); O. Michael Colvin, Chapel Hill, NC (US); Monroe E. Wall, Chapel Hill, NC (US); Mansukh C. Wani, Durham, NC (US); Govindarajan Manikumar, Raleigh, NC (US); Yves Pommier, Bethesda, MD (US)

(73) Assignees: Research Triangle Institute, Research Triangle Park, NC (US); Duke University, Durham, NC (US); National Institutes of Health, Rockville, MD (US)

( * ) Notice: Subject to any disclaimer, the term of this patent is extended or adjusted under 35 U.S.C. 154(b) by 0 days.

(21) Appl. No.: 09/712,912

(22) Filed: Nov. 16, 2000

(51) Int. Cl.⁷ ............................................... A61K 31/44
(52) U.S. Cl. ........................... 514/283; 514/2; 514/279
(58) Field of Search ................................ 514/279, 283, 514/2

(56) References Cited

U.S. PATENT DOCUMENTS

| | | | | |
|---|---|---|---|---|
| 4,399,282 A | * | 8/1983 | Miyasaka et al. | 546/48 |
| 4,943,579 A | | 7/1990 | Vishnuvajjala et al. | 514/283 |
| 4,981,968 A | | 1/1991 | Wall et al. | 544/361 |
| 5,049,668 A | | 9/1991 | Wall et al. | 540/481 |
| 5,122,526 A | | 6/1992 | Wall et al. | 514/253 |
| 5,180,722 A | | 1/1993 | Wall et al. | 514/219 |
| 5,932,588 A | | 8/1999 | Wall et al. | 514/279 |
| 5,985,888 A | | 11/1999 | Wall et al. | |

OTHER PUBLICATIONS

Mohit S. Kasibhatla, et al., Glutathione–Mediated Sensitivity to the Campthothecins, Pharmacology and Experimental Therapeutics, Proceedings of the American Association for Cancer Research, vol. 41, Mar. 2000.

* cited by examiner

*Primary Examiner*—Dwayne Jones
(74) *Attorney, Agent, or Firm*—Oblon, Spivak, McClelland, Maier & Neustadt, P.C.

(57) ABSTRACT

Camptothecin compounds which are effective anti-tumor compounds are disclosed. These conjugates inhibit the enzyme topoisomerase I and enhance the stability of the topoisomerase I-DNA cleavable complex.

8 Claims, 7 Drawing Sheets

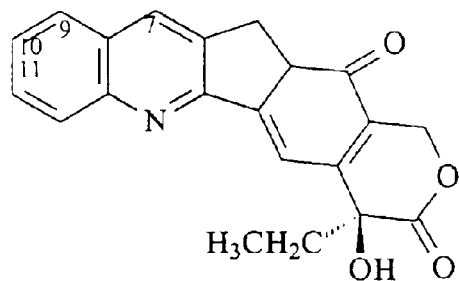
20(S)-camptothecin (CPT)
10,11-methylenedioxy-20(S)-camptothecin (MDC): 10,11 = -O-CH$_2$-O-
Figure 1: Structure of campthothecin (CPT) and methylenedioxycamptothecin (MDC)
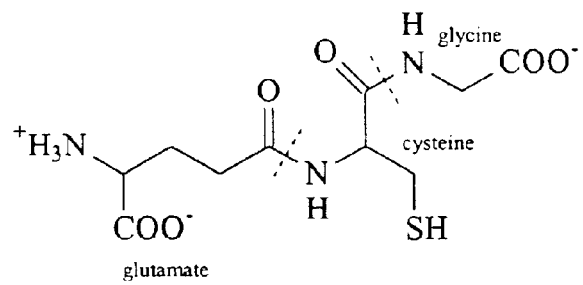
Figure 2: Structure of the tripeptide glutathione (GSH)

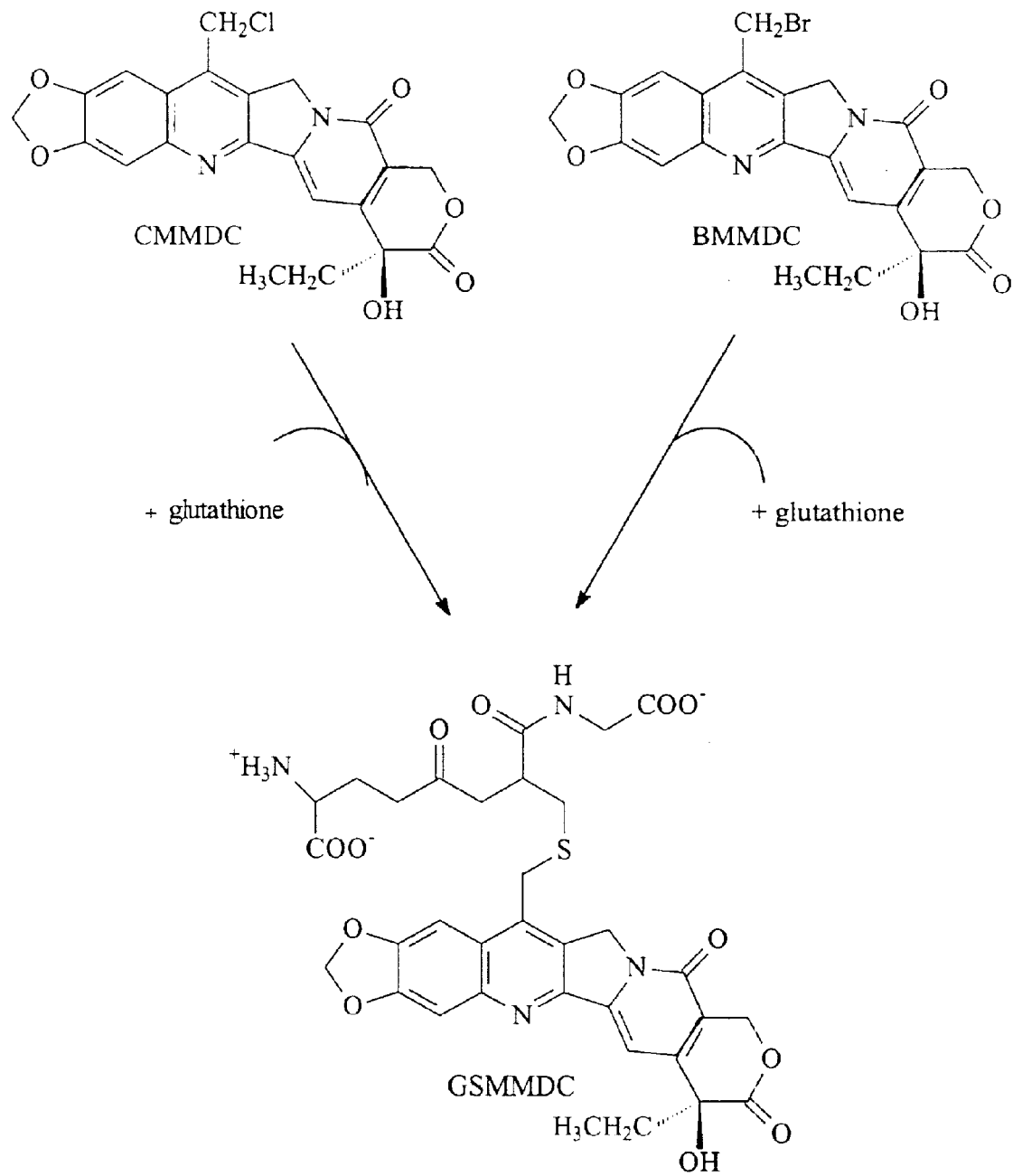
Figure 3. Reaction of 7-chloromethyl-10,11-methylenedioxy-20(S)-camptothecin (CMMDC) or 7-bromomethyl-10,11-methylenedioxy-20(S)-camptothecin (BMMDC) with glutahione yields the conjugate 7-(methyl-S-glutathionyl)-10,11-methylenedioxycamptothecin (GSMMDC).

Figure 5:

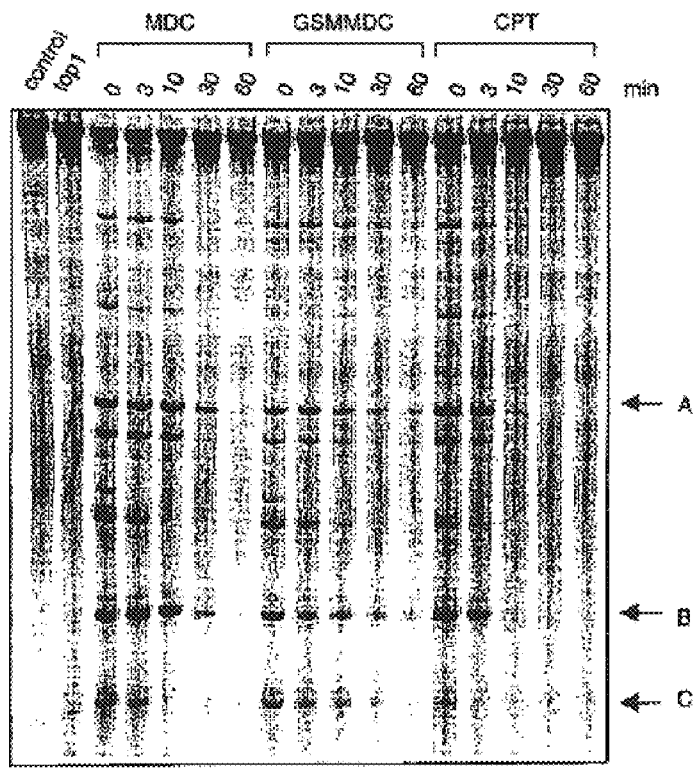

Reversal Kinetics of DNA cleavage produced by human top1 in pSK DNA
(GSMMDC = 7-chloromethyl-10,11-methylenedioxycamptothecin;
MDC = 10,11-methylenedioxycamptothecin; CPT = camptothecin)

Reactions for 15 min at room temperature
Followed by addition of 0.35 M NaCl (final concentration) for the indicated times.
Reactions stopped with 0.5% SDS; Sequencing gel Next figure shows the quantitation after PhosphorImager analysis Reversal Kinetics of DNA cleavage produced by human t p1 in pSK DNA
(GSMMDC = 7-chloromethyl-10,11-methylenedioxycampt thecin;
MDC = 10,11-methylenedioxycamptothecin; CPT = camptothecin)

Quantitation by Phospholmager of previous gel

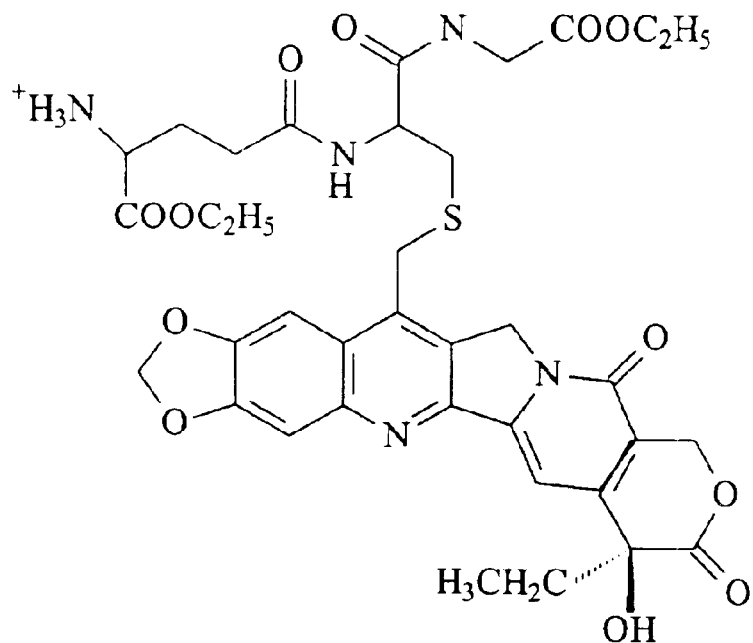
Figure 8: Diethylester of GSMMDC
$R_1 = CH_3-CO-$; $R_2 = -OH$
$R_1 = H$; $R_2 =$ glycine
$R_1 =$ amino acid; $R_2 =$ amino acid
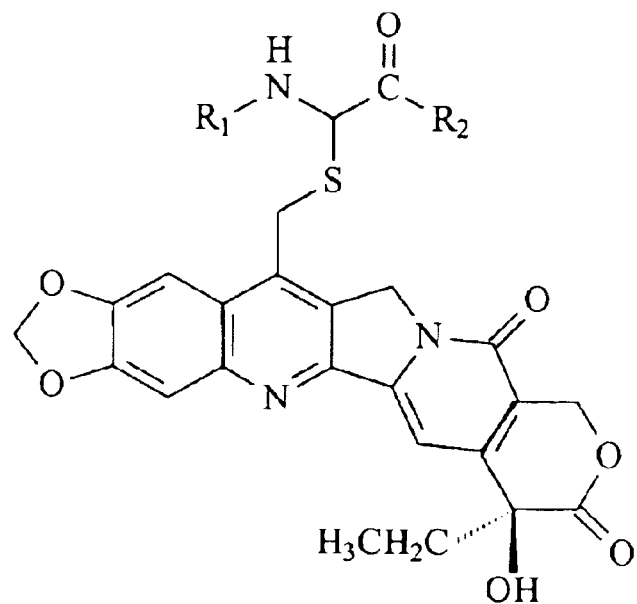
Figure 9: Camptothecin derivatives based on cysteinyl-conjugate

CAMPTOTHECIN COMPOUNDS WITH A THIOETHER GROUP

BACKGROUND OF THE INVENTION

1. Field of the Invention

This invention relates to camptothecin compounds which inhibit the enzyme topoisomerase I and have anticancer activity. This invention is also related to the treatment of leukemia, solid tumors and brain glioma in mammals using the conjugates.

2. Background of the Invention

Camptothecin (CPT) is a naturally occurring cytotoxic alkaloid which is known to inhibit the enzyme topoisomerase I and is a potent anti-tumor agent. Camptothecin compounds have the general ring structure shown below.

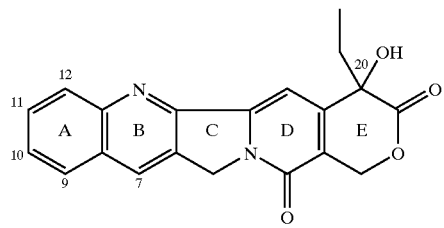

Camptothecin was first isolated from the wood and bark of *Camptotheca acuminata* by Wall et al. (Wall et al., 1966, J. Am. Chem. Soc., 88:3888).

Major synthetic efforts have been directed to derivatizing the A-ring and/or the B-ring attempting to improve cytotoxic activity and water-solubility.

U.S. Pat. No. 4,894,456 describes methods of synthesizing camptothecin compounds which act as inhibitors of topoisomerase I and are effective in the treatment of leukemia (L-1210). U.S. Pat. No. 5,225,404 discloses methods of treating colon tumors with camptothecin compounds. U.S. Pat. No. 4,894,456 describes methods of synthesizing camptothecin compounds which act as inhibitors of topoisomerase I and are effective in the treatment of leukemia (L-1210). U.S. Pat. No. 5,225,404 discloses methods of treating colon tumors with camptothecin compounds.

Numerous camptothecin compounds and their use as inhibitors of topoisomerase I are taught by U.S. Pat. No. 5,053,512; U.S. Pat. No. 4,981,968; U.S. Pat. No. 5,049,668; U.S. Pat. No. 5,106,742; U.S. Pat. No. 5,180,722; U.S. Pat. No. 5,244,903; U.S. Pat. No. 5,227,380; U.S. Pat. No. 5,122,606; U.S. Pat. No. 5,122,526; and U.S. Pat. No. 5,340,817. Analogs of camptothecin which show antiproliferative activity against human tumors both in vitro and in vivo have been developed and are described in U.S. Pat. Nos. 4,981,968; 5,049,668 and 5,122,526.

Brangi et al., *Cancer Research*, 59, 5938–5946 (1999), reports an investigation of camptothecin resistance in cancer cells and reports the compound difluoro-10,11-methylenedioxy-20(S)-camptothecin.

Of particular interest is the production of 10,11-methylenedioxy-20(S)-camptothecin (MDC) and analogs (U.S. Pat. No. 5,180,722) and alkylating analogs (U.S. Pat. No. 5,985,888). These MDC analogs have been shown to be highly active when tested against a number of human cancer cell lines (O'Connor, 1990 #2346; Adams et al.).

In order to increase the lifetime of the cleavable complexes with MDC, an analog was developed containing an alkylating chloromethyl group: 7-chloromethyl-10,11-methylenedioxy-20(S)-camptothecin, CMMDC (U.S. Pat. No. 5,559,235). This analog has been shown to alkylate the purine immediately 3' to the cleavage site resulting in enhanced toxicity (Pommier, 1995 #2174; Valenti, 1997 #2344). The 7-bromomethyl-10,11-methylenedioxy-20(S)-camptothecin has also been described (U.S. Pat. No. 5,985,888) but probably due to the extreme reactivity of the bromomethyl group is not suitable for in vivo studies.

Glutathione (FIG. 2) is a tripeptide of glutamic acid, cysteine and glycine and found in high concentration in most normal cells and is often elevated in tumor tissue. In cancer cells, glutathione appears to play an important role in resistance to chemotherapy (Tew, 1994 #1038; Colvin, 1993 #628). For example, the chemotherapeutic alkylating agents such as cyclophosphamide, cisplatinum and BCNU are inactivated by covalent conjugation with glutathione to form thioether metabolites. This can occur spontaneously or through the action of the glutathione S-transferase enzymes. These transferases are often overexpressed in drug-resistant cells (Tew, 1994 #1038). Therefore glutathione conjugation results in chemical inactivation of the drug as well as increased export of the drug from the cell leading to resistance.

Peptide derivatives of camptothecin have been made. For example, a number of derivatives created by formation of amide linkages between the carboxylate of amino acids and peptides and the amine of 9-amino-camptothecins have been proposed to improve solubility (U.S. Pat. No. 5,180,722). A derivative containing a γ-glutamyl-linkage to the 9-amino position has been patented as a prodrug to deliver camptothecin to cells which express γ-glutamyltranspeptidase (U.S. Pat. No. 5,854,006). Peptide derivatives have also been prepared as linker arms between camptothecin and polymers to improve drug delivery (U.S. Pat. No. 5,892,043).

Formation of glutathione conjugates of anticancer drugs has been reported in some instances to result in inactivation or increased transport of the drugs out of the cell. There are however several examples of glutathione conjugates which appear to bind to and inhibit enzymes and therefore be potentially useful therapeutic agents. The glutathione conjugate of the anticancer drugs doxorubicin and daunorubicin (Gaudiano et al, *JACS* 1994, 116, 6537; claimed in U.S. Pat. No. 5,646,177) inhibit some of the drug efflux proteins and used in combination with other agents may be beneficial therapeutic agents (Asakura, 1997 #1749; Priebe, 1998 #2179).

Another anticancer agent has been designed as a glutathione conjugate analog. This agent, the peptidomimetic γ-glutamyl-S-(benzyl)cysteinyl-R(−)-phenyl-glycine (TER 117) is designed to inhibit glutathione 5-transferase. In vivo activity against cancer cell lines is realized when the diethyl ester derivative (TER199) was prepared (Morgan, 1996 #2348).

A glutathione conjugate has also been shown to bind to a DNA-dependent protein kinase (Shen, 1999 #2349). This kinase can bind DNA (structural similarities to topoI?)

A need continues to exist, however, for camptothecin compounds having improved biological activity. The present invention is directed to camptothecin compound which may be prepared by the reaction of a cysteine containing group with an alkylating camptothecin.

SUMMARY OF THE INVENTION

Accordingly, one object of the present invention is to provide novel camptothecin compounds.

Another object of the present invention is to provide a method of treating leukemia or solid tumors in a mammal in need thereof by administration of a camptothecin-peptide conjugate.

Another object of the present invention is to provide a method of inhibiting the enzyme topoisomerase I and/or alkylating DNA of associated DNA-topoisomerase I by contacting a DNA-topoisomerase I complex with a camptothecin-peptide conjugate.

Another object of the present invention is to provide a method of stabilizing the enzyme topoisomerase I and/or alkylating DNA of associated DNA-topoisomerase I by contacting a DNA-topoisomerase I complex with a camptothecin-peptide conjugate.

These and other objects are made possible by the following camptothecin compounds which have combined topoisomerase I inhibiting and DNA-topoisomerase I cleavable complex stabilizing properties, of the formula

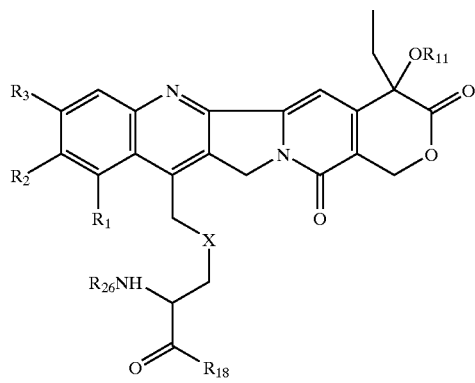

wherein $R_1$ and $R_2$, are each independently $NO_2$, $NH_2$, H, F, Cl, Br, I, COOH, OH, O—$C_{1-6}$ alkyl, SH, S—$C_{1-6}$ alkyl, CN, NH—$C_{1-6}$ alkyl, N($C_{1-6}$ alkyl)$_2$, CHO, $C_{1-8}$ alkyl, $N_3$, —Z—$(CH_2)_a$—N—$((CH_2)_bOH)_2$, wherein Z is selected from the group consisting of O, NH and S, and a and b are each independently an integer of 2 or 3, —Z—$(CH_2)_a$—N—$(C_{1-6}$ alkyl)$_2$ wherein Z is selected from the group consisting of O, NH and S, and a is an integer of 2 or 3, —$CH_2NR_4R_5$ where (a) $R_4$ and $R_5$ are, independently, hydrogen, $C_{1-6}$ alkyl, $C_{3-7}$ cycloalkyl, $C_{3-7}$ cycloalkyl-$C_{1-6}$ alkyl, $C_{2-6}$ alkenyl, hydroxy-$C_{1-6}$ alkyl, $C_{1-6}$ alkoxy-$C_{1-6}$ $COR_6$ where $R_6$ is hydrogen, $C_{1-6}$ alkyl, perhalo-$C_{1-6}$ alkyl, $C_{3-7}$ cycloalkyl, $C_{3-7}$ cycloalkyl-$C_{1-6}$ alkyl, $C_{2-6}$ alkenyl, hydroxy-$C_{1-6}$ alkyl, $C_{1-6}$ alkoxy, $C_{1-6}$ alkoxy-$C_{1-6}$ alkyl, or (b) $R_4$ and $R_5$ taken together with the nitrogen atom to which they are attached form a saturated 3–7 membered heterocyclic ring which may contain a O, S or $NR_7$ group, where $R_7$ is hydrogen, $C_{1-6}$ alkyl, perhalo-$C_{1-6}$ alkyl, aryl, aryl substituted with one or more groups selected from the group consisting of $C_{1-6}$ alkyl, halogen, nitro, amino, $C_{1-6}$ alkylamino, perhalo-$C_{1-6}$ alkyl, hydroxy-$C_{1-6}$ alkyl, $C_{1-6}$ alkoxy, $C_{1-6}$ alkoxy-$C_{1-6}$ alkyl and —$COR_8$ where $R_8$ is hydrogen, $C_{1-6}$ alkyl perhalo-$C_{1-6}$ alkyl, $C_{1-6}$ alkoxy, aryl, and aryl substituted with one or more $C_{1-6}$ alkyl, perhalo-$C_{1-6}$ alkyl, hydroxy-$C_{1-6}$ alkyl, or $C_{1-6}$ alkoxy-$C_{1-6}$ alkyl groups;

$R_3$ is H; or or $R_2$ and $R_3$ combine to form a ring

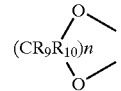

where $R_9$ and $R_{10}$ are each independently H or F and n is an integer of 1 or 2;

$R_{11}$ is H, or $C(O)$—$(CH_2)_m$—$NR_{12}R_{13}$, where m is an integer of 1–6 or —$C(O)CHR_{14}NR_{12}R_{13}$, where $R_{14}$ is the side chain of one of the naturally occurring α-amino acids, $R_{12}$ and $R_{13}$ are, independently, hydrogen, $C_{1-8}$ alkyl or —$C(O)CHR_{15}NR_{16}R_{17}$, where $R_{15}$ is the side chain of one of the naturally occurring α-amino acids and $R_{16}$ and $R_{17}$ are each independently hydrogen or $C_{1-8}$ alkyl;

$R_{18}$ is $OR_{19}$ or $R_{19}OC(O)$—$(CH_2)_m$—$NR_{20}$, or $R_{21}OC(O)CHR_{22}NR_{20}$, where $R_{19}$ is H or $C_{1-6}$ alkyl, m is an integer of 1–6, $R_{22}$ is the side chain of one of the naturally occurring α-amino acids, $R_{20}$ is hydrogen, $C_{1-8}$ alkyl or —$C(O)CHR_{23}NR_{24}R_{25}$, where $R_{23}$ is the side chain of one of the naturally occurring α-amino acids and $R_{24}$ and $R_{25}$ are each independently hydrogen or $C_{1-8}$ alkyl;

$R_{26}$ is H or

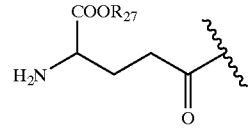

where $R_{27}$ is H or $C_{1-6}$ alkyl; and
X is S or O,
or a pharmaceutically acceptable salt thereof.

BRIEF DESCRIPTION OF THE DRAWINGS

A more complete appreciation of the invention and many of the attendant advantages thereof will be readily obtained as the same become better understood by reference to the following detailed description when considered in connection with the accompanying drawings, wherein:

FIG. 1. Structure of camptothecin (CPT) and methylenedioxycamptothecin (MDC);

FIG. 2. Structure of the tripeptide glutathione (GSH);

FIG. 3. Formation of GSMMDC;

FIG. 5. Reversal kinetics of DNA cleavage produced by human topI in pSK DNA;

FIG. 8. Diethylester of GSMMDC; and

FIG. 9. Camptothecin derivatives based on cysteinyl conjugate.

DETAILED DESCRIPTION OF THE PREFERRED EMBODIMENTS

Figure 4:
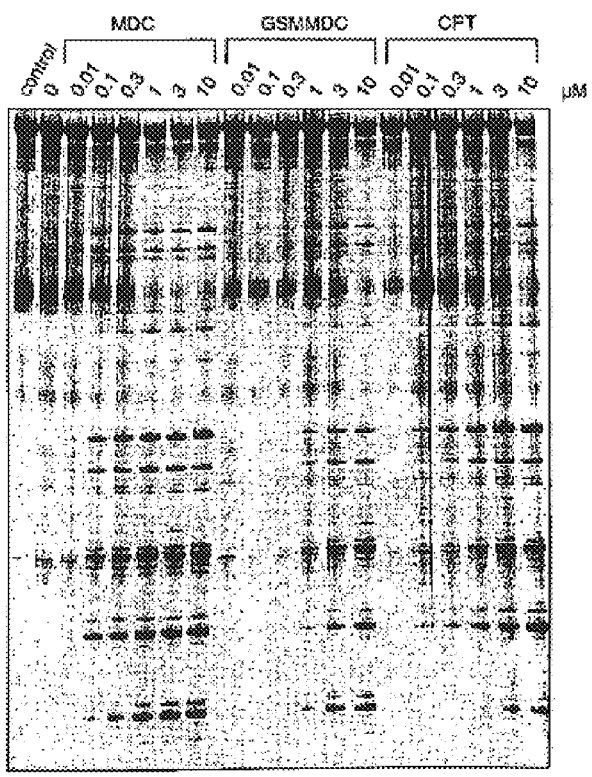
FIG. 4. DNA cleavage produced by human topI in pSK DNA.

Camptothecin compounds have an asymmetric carbon atom at the 20-position making two enantiomeric forms, i.e., the (R) and the (S) configurations, possible. The compounds of this invention include both enantiomeric forms, entantiomerically pure or enriched (e.g. ee>80%, more preferably >90>, more preferably >95%, even more preferably >99%) and any combinations or mixtures of these forms. The invention also includes other forms of the compounds including solvates, hydrates, polymorphs, salts, etc. Particularly preferred conjugates are those having the (S) configuration at the 20-position of the CPT moiety.

The term "alkyl" as used herein means a straight-chain or branched chain alkyl group with 1–30, preferably 1–18 carbon atoms, more preferably 1–8 carbon atoms, including methyl, ethyl, n-propyl, isopropyl, n-butyl, isobutyl, sec-butyl, tert-butyl, n-pentyl, isopentyl, n-hexyl, n-heptyl, n-octyl, 2-ethylhexyl, n-nonyl, n-decyl, undecyl, dodecyl, myristyl, heptadecyl and octadecyl groups. The term "alkyl" also includes cycloalkyl groups such as cyclopropyl, cyclopentyl, cyclohexyl, cycloheptyl and cyclooctyl groups.

The term "aryl" as used herein means a carbocyclic aromatic ring having 6–18 carbon atoms, preferably 6–10 carbon atoms in the aromatic ring structure. The aromatic rings may be substituted by one or more alkyl group, preferably alkyl groups having 1–10 carbon atoms. A particularly preferred aryl group is phenyl.

The term "aralkyl" as used herein means a straight-chain or branched chain alkyl group as defined above for the term "alkyl" bonded to an aryl group as defined above for the term "aryl". Preferred aralkyl groups are benzyl, phenethyl, etc.

As used herein, the term "acyl" means formyloxy and acyl moieties derived from aromatic carboxylic acids, heterocyclic carboxylic acids, aralkyl carboxylic acids, as well as alkyl and aromatic sulfonic acids. The alkyl groups of these acyloxy moieties may be a straight-chain or branched-chain alkyl group with 1–7 carbon atoms. Additionally, the acyl moiety may contain one or more unsaturated carbon-carbon bonds and may also carry one or more substituents such as halogen, amino and hydroxyl groups.

The terms "sulfhydryl-containing amino acid" or "sulfhydryl-containing peptide" as used herein refer to an amino acid or peptide having at least one SH group, such as cysteine or cysteine containing peptides. The sulfhydryl-containing amino acids or peptides can be naturally occurring or can be synthesized by any of the techniques that are known to those skilled in the art.

The present invention is directed to a camptothecin compound

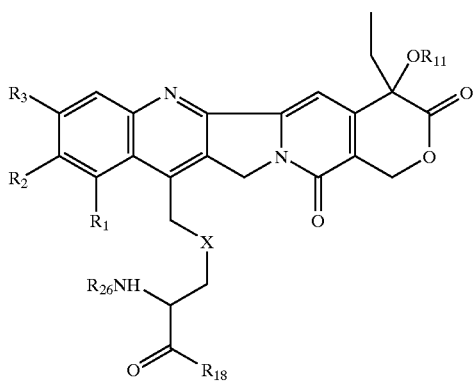

wherein $R_1$ and $R_2$, are each independently
$NO_2$, $NH_2$, H, F, Cl, Br, I, COOH, OH, O—$C_{1-6}$ alkyl, SH, S—$C_{1-6}$ alkyl, CN, NH—$C_{1-6}$ alkyl, N($C_{1-6}$ alkyl)$_2$, CHO, $C_{1-8}$ alkyl, $N_3$, —Z—$(CH_2)_a$—N—$((CH_2)_bOH)_2$, wherein Z is selected from the group consisting of O, NH and S, and a and b are each independently an integer of 2 or 3, —Z—$(CH_2)_a$—N—$(C_{1-6}$ alkyl$)_2$ wherein Z is selected from the group consisting of O, NH and S, and a is an integer of 2 or 3, —$CH_2NR_4R_5$, where (a) $R_4$ and $R_5$ are, independently, hydrogen, $C_{1-6}$ alkyl, $C_{3-7}$ cycloalkyl, $C_{3-7}$ cycloalkyl-$C_{1-6}$ alkyl, $C_{2-6}$ alkenyl, hydroxy-$C_{1-6}$ alkyl, $C_{1-6}$ alkoxy-$C_{1-6}$ $COR_6$ where $R_6$ is hydrogen, $C_{1-6}$ alkyl, perhalo-$C_{1-6}$ alkyl, $C_{3-7}$ cycloalkyl, $C_{3-7}$ cycloalkyl-$C_{1-6}$ alkyl, $C_{2-6}$ alkenyl, hydroxy-$C_{1-6}$ alkyl, $C_{1-6}$ alkoxy, $C_{1-6}$ alkoxy-$C_{1-6}$ alkyl, or (b) $R_4$ and $R_5$ taken together with the nitrogen atom to which they are attached form a saturated 3–7 membered heterocyclic ring which may contain a O, S or $NR_7$ group, where $R_7$ is hydrogen, $C_{1-6}$ alkyl, perhalo-$C_{1-6}$ alkyl, aryl, aryl substituted with one or more groups selected from the group consisting of $C_{1-6}$ alkyl, halogen, nitro, amino, $C_{1-6}$ alkylamino, perhalo-$C_{1-6}$ alkyl, hydroxy-$C_{1-6}$ alkyl, $C_{1-6}$ alkoxy, $C_{1-6}$ alkoxy-$C_{1-6}$ alkyl and —$COR_8$ where $R_8$ is hydrogen, $C_{1-6}$ alkyl perhalo-$C_{1-6}$ alkyl, $C_{1-6}$ alkoxy, aryl, and aryl substituted with one or more $C_{1-6}$ alkyl, perhalo-$C_{1-6}$ alkyl, hydroxy-$C_{1-6}$ alkyl, or $C_{1-6}$ alkoxy-$C_{1-6}$ alkyl groups;

$R_3$ is H; or
or $R_2$ and $R_3$ combine to form a ring

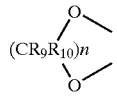

where $R_9$ and $R_{10}$ are each independently H or F and n is an integer of 1 or 2;

$R_{11}$ is H, or $C(O)$—$(CH_2)_m$—$NR_{12}R_{13}$, where m is an integer of 1–6 or —$C(O)CHR_{14}NR_{12}R_{13}$, where $R_{14}$ is the side chain of one of the naturally occurring α-amino acids, $R_{12}$ and $R_{13}$ are, independently, hydrogen, $C_{1-8}$ alkyl or —$C(O)CHR_{15}NR_{16}R_{17}$, where $R_{15}$ is the side chain of one of the naturally occurring α-amino acids and $R_{16}$ and $R_{17}$ are each independently hydrogen or $C_{1-8}$ alkyl;

$R_{18}$ is $OR_{19}$ or $R_{19}OC(O)$—$(CH_2)_m$—$NR_{20}$, or $R_{21}OC(O)CHR_{22}NR_{20}$, where $R_{19}$ is H or $C_{1-6}$ alkyl, m is an integer of 1–6, $R_{22}$ is the side chain of one of the naturally occurring α-amino acids, $R_{20}$ is hydrogen, $C_{1-8}$ alkyl or —$C(O)CHR_{23}NR_{24}R_{25}$, where $R_{23}$ is the side chain of one of the naturally occurring α-amino acids and $R_{24}$ and $R_{25}$ are each independently hydrogen or $C_{1-8}$ alkyl;

$R_{26}$ is H or

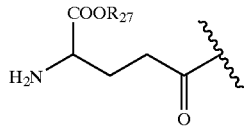

where $R_{27}$ is H or $C_{1-6}$ alkyl; and
X is S or O,
or a pharmaceutically acceptable salt thereof.

In the compound according to the present invention, it will be appreciated by those of ordinary skill in the art that when the group $R_{18}$ is other than OH, the group $R_{18}$ is attached via an amide linkage formed between the carbonyl of the cystine residue and the amino group of $R_{18}$.

According to the present invention, the $C_7$ position is substituted with a residue which may contain one or two carboxylic acid and/or carboxylic ester groups. Within the context of the present invention, the camptothecin compounds of the present invention may specifically contain two carboxylic acid groups (diacid), two carboxylic ester groups (diester), or a carboxylic acid group and a carboxylic ester group (half acid, half ester). In addition, when the campothecin compound of the present invention contains two carboxylic acid groups, one or both of the carboxylic acid groups may be in the form of a salt (such as, but not limited to $Na^+$, $K^+$, $Li^+$, $Mg^{+2}$, $Ca^{+2}$) providing for a diacid salt or half acid, half salt.

This invention describes the formation of conjugates of camptothecin, or camptothecin derivatives, and sulfhydryl-containing amino acids or peptides, or derivatives thereof. The conjugates may be prepared by reacting a 7-substituted alkylating camptothecin, or derivative thereof, with the thiolate of a sulfhydryl-containing amino acid or peptide, or derivative thereof.

Camptothecin compounds which may be used to form the conjugates of the present invention include 20(S)-CPT and derivatives thereof in which the A ring is unsubstituted or there is a substituent at the 9-, 10-, and 11-positions or a combination thereof or the 9- and 10,11-positions. Suitable compounds have the structure shown below:

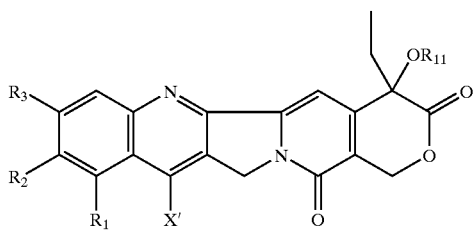

wherein $R_1$ and $R_2$, are each independently
$NO_2$, $NH_2$, H, F, Cl, Br, I, COOH, OH, O—$C_{1-6}$ alkyl, SH, S—$C_{1-6}$ alkyl, CN, NH—$C_{1-6}$ alkyl, $N(C_{1-6}$ alkyl$)_2$, CHO, $C_{1-8}$ alkyl, $N_3$, —Z—$(CH_2)_a$—N—$((CH_2)_bOH)_2$, wherein Z is selected from the group consisting of O, NH and S, and a and b are each independently an integer of 2 or 3, —Z—$(CH_2)_a$—N—$(C_{1-6}$ alkyl$)_2$ wherein Z is selected from the group consisting of O, NH and S, and a is an integer of 2 or 3, —$CH_2NR_4R_5$, where (a) $R_4$ and $R_5$ are, independently, hydrogen, $C_{1-6}$ alkyl, $C_{3-7}$ cycloalkyl, $C_{3-7}$ cycloalkyl-$C_{1-6}$ alkyl, $C_{2-6}$ alkenyl, hydroxy-$C_{1-6}$ alkyl, $C_{1-6}$ alkoxy-$C_{1-6}$ $COR_6$ where $R_6$ is hydrogen, $C_{1-6}$ alkyl, perhalo-$C_{1-6}$ alkyl, $C_{3-7}$ cycloalkyl, $C_{3-7}$ cycloalkyl-$C_{1-6}$ alkyl, $C_{2-6}$ alkenyl, hydroxy-$C_{1-6}$ alkyl, $C_{1-6}$ alkoxy, $C_{1-6}$ alkoxy-$C_{1-6}$ alkyl, or (b) $R_4$ and $R_5$ taken together with the nitrogen atom to which they are attached form a saturated 3–7 membered heterocyclic ring which may contain a O, S or $NR_7$ group, where $R_7$ is hydrogen, $C_{1-6}$ alkyl, perhalo-$C_{1-6}$ alkyl, aryl, aryl substituted with one or more groups selected from the group consisting of $C_{1-6}$ alkyl, halogen, nitro, amino, $C_{1-6}$ alkylamino, perhalo-$C_{1-6}$ alkyl, hydroxy-$C_{1-6}$ alkyl, $C_{1-6}$ alkoxy, $C_{1-6}$ alkoxy-$C_{1-6}$ alkyl and —$COR_8$ where $R_8$ is hydrogen, $C_{1-6}$ alkyl perhalo-$C_{1-6}$ alkyl, $C_{1-6}$ alkoxy, aryl, and aryl substituted with one or more $C_{1-6}$ alkyl, perhalo-$C_{1-6}$ alkyl, hydroxy-$C_{1-6}$ alkyl, or $C_{1-6}$ alkoxy-$C_{1-6}$ alkyl groups;

$R_3$ is H; or
or $R_2$ and $R_3$ combine to form a ring

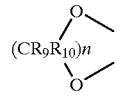

where $R_9$ and $R_{10}$ are each independently H or F and n is an integer of 1 or 2;

$R_{11}$ is H, or C(O)—$(CH_2)_m$—$NR_{12}R_{13}$, where m is an integer of 1–6 or —C(O)$CHR_{14}NR_{12}R_{13}$, where $R_{14}$ is the side chain of one of the naturally occurring α-amino acids, $R_{12}$ and $R_{13}$ are, independently, hydrogen, $C_{1-8}$ alkyl or —C(O)$CHR_{15}NR_{16}R_{17}$, where $R_{15}$ is the side chain of one of the naturally occurring α-amino acids and $R_{16}$ and $R_{17}$ are each independently hydrogen or $C_{1-8}$ alkyl; and X' is $CH_2$—L where L is a leaving group.

Suitable side chains $R_{14}$, $R_{15}$, $R_{22}$ and $R_{23}$ are the side chains of the amino acids glycine, alanine, valine, leucine, isoleucine, phenylalanine, tyrosine, tryptophan, lysine, arginine, histidine, aspartate, glutamate, asparagine, glutamine, cysteine and methionine. Particularly preferred esters are glycinate esters. The esters may be prepared by the method described in U.S. Pat. No. 4,943,579 which is incorporated herein by reference for a more complete description of the process of preparing the esters and for a description of suitable esters formed by the process.

In the structure shown above, X' is —$CH_2$—L, where L is defined as follows: an electronegative functionality with the ability to be readily displaced by nucleophilic species. In the present invention, L may represent halogen (Cl, Br or I), or any OY group, where Y is a species which renders OY a leaving group toward nucleophilic displacement. Suitable Y groups include, but are not limited to, alkyl-C(=O)—, aryl-C(=O)—, alkyl-$SO_2$—, perfluoroalkyl-$SO_2$— and aryl-$SO_2$—, where alkyl and aryl are as defined above.

Compounds in which L is Br or I are readily prepared from the compound in which L is Cl by simple halide exchange employing LiBr or LiI in dimethylformamide (DMF) solution (Larock, R. C., Comprehensive Organic Transformations, VCH Publishers, Inc., p. 337, N.Y. 1989).

Camptothecin compounds having the group —$CH_2$—L at $C_7$ may be generally prepared by a method analogous to the process described by Luzzio et al. (European Patent Application 540099A1; J. Med. Chem., 1995, 38:395) and in U.S. Pat. No. 5,053,512 and U.S. Pat. No. 5,053,512 involving Friedlander condensation of the appropriate synthon and a tricyclic ketone.

Alternatively, the 7-methyl compounds (L is H) can be prepared either by a Friedlander reaction employing the corresponding acetophenone, or by a free radical alkylation reaction (Sawada et al., 1991, Chem. Pharm. Bull., 39:2574). Free radical bromination of 7-methyl substrates can be accomplished by employing N-bromosuccinimide (NBS) in acetic acid (HOAc) under catalysis by benzoyl peroxide to give compounds in which L is Br.

Many CPT compounds can be derivatized at the 7-position with —$CH_2$—L. CPT compounds suitable for derivatization are described, for example, in U.S. Pat. No. 4,894,456, U.S. Pat. No. 4,981,968, U.S. Pat. No. 5,053,512, U.S. Pat. No. 5,049,668, U.S. Pat. No. 5,106,742, U.S. Pat. No. 5,180,722, U.S. Pat. No. 5,244,903, U.S. Pat. No. 5,227,380, U.S. Pat. No. 5,122,606, U.S. Pat. No. 5,122,526, U.S. Pat. No. 5,225,404, U.S. Pat. No. 4,914,205, U.S. Pat. No. 4,545,880, U.S. Pat. No. 4,604,463, U.S. Pat. No. 4,473,692 and U.S. Pat. No. 4,031,098.

Preferred camptothecin compounds having the group —CH$_2$—L at C$_7$ which may be used to synthesize the conjugate of the invention are CPT compounds in which two substituents on the A ring are joined together to form a bifunctional substituent such as the methylenedioxy or difluromethylenedioxy groups. Methylenedioxy or difluromethylenedioxy substituents may be bonded to any two consecutive positions in the A ring, for example, the 9,10 or 10,11 positions. Analogs containing the 10,11-methylenedioxy moiety may be prepared by the method described in U.S. Pat. No. 4,981,968 and U.S. Pat. No. 5,180,722 which are incorporated herein by reference for a more complete description of the process of preparing the precursor CPT analogs and for a description of suitable precursor CPT analogs formed by the process.

Analogs containing the 10,11-difluoromethylenedioxy moiety may be prepared in a manner analogous to conventional methods known to those of ordinary skill in the art such as those described in co-pending application U.S. Ser. No. 09/474,758, filed on Dec. 29, 1999 the relevant portions of which describe the preparation of 10,11-difluoromethylenedioxy CPT compounds being incorporated herein by reference.

Specific non-limiting examples of 10,11-substituted precursor CPT compounds having an alkylating group at C$_7$ which may be used to synthesize the conjugates of the invention include 7-chloromethyl-10,11-methylenedioxy-20-(S)-camptothecin; 7-bromomethyl-10,11-methylenedioxy-20-(S)-camptothecin and 7-hydroxymethyl-10,11-methylenedioxy-20-(S)-camptothecin.

Additional specific non-limiting examples further include 7-chloromethyl-10,11-difluoromethylenedioxy-20-(S)-camptothecin; 7-bromomethyl-10,11-difluoromethylenedioxy-20-(S)-camptothecin and 7-hydroxymethyl-10,11-difluoromethylenedioxy-20-(S)-camptothecin;

Additional specific non-limiting examples further include 7-bromomethyl-20-(S)-camptothecin; 7-chloromethyl-20-(S)-camptothecin; 7-hydroxymethyl-20-(S)-camptothecin.

The preparation of 7-hydroxymethyl-10,11-methylenedioxy-20(S)-CPT and 7-bromomethyl-10,11-methylenedioxy-20(S)-CPT is also described in Examples 1 and 2.

Additional CPT compounds which may be used to prepare the compounds of the present invention may also include C$_{20}$ OH CPT compounds prepared by conventional methods known to those of ordinary skill in the art, such as that described by U.S. Pat. No. 5,122,526. The lactone ring of the camptothecin compounds shown above may be opened by alkali metal or alkaline earth metal bases (MOH), for example, sodium hydroxide or calcium hydroxide, to form alkali metal or alkaline earth metal salts of the open ring salt form of the camptothecin compounds, illustrated for example by the following CPT compound.

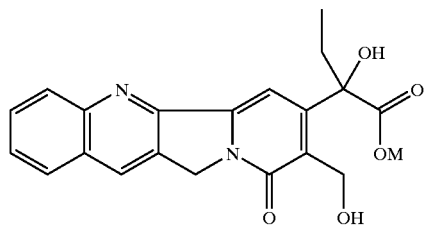

Open ring compounds generally have better solubility in water. The group M may also be any pharmaceutically acceptable cation, obtained either directly by ring opening or by cation exchange of a ring open salt. Suitable groups M include Li$^+$, Na$^+$, K$^+$ and Mg$^{2+}$.

Esterification with an amino acid at C$_{20}$ is possible by conventional methods known to those of ordinary skill in the art.

The sulfhydryl-containing amino acids or sulfhydryl-containing peptides which may be used to prepare the compounds of the present invention include those compounds having the formula:

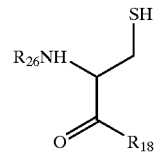

where, R$_{18}$ s OR$_{19}$ or R$_{19}$OC(O)—(CH$_2$)$_m$—NR$_{20}$, or R$_{21}$OC(O)CHR$_{22}$NR$_{20}$, where R$_{19}$ is H or C$_{1-6}$ alkyl, m is an integer of 1–6, R$_{22}$ is the side chain of one of the naturally occurring α-amino acids, R$_{20}$ is hydrogen, C$_{1-8}$ alkyl or —C(O)CHR$_{23}$NR$_{24}$R$_{25}$, where R$_{23}$ is the side chain of one of the naturally occurring α-amino acids and R$_{24}$ and R$_{25}$ are each independently hydrogen or C$_{1-8}$ alkyl; and R$_{26}$ is H or

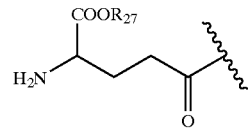

where R$_{27}$ is H or C$_{1-6}$ alkyl,

A particularly preferred sulfhydryl-containing peptide is glutathione.

The compounds of the present invention may be prepared by conventional methods known to those of ordinary skill in the art without undue experimentation.

The formation of a conjugate of camptothecin formed by the reaction of 7-chloromethyl- or 7-bromomethyl-10,11-methylenedioxy-20(S)-camptothecin with the thiolate of the cysteinyl residue of the tripeptide glutathione is shown in FIG. 3. The 7-methyl-S-glutathionyl-10,11-methylenedioxy-20(S)camptothecin conjugate (GSMMDC) is also shown in FIG. 3. GSMMDC shows enhanced ability to stabilize the DNA-topoisomerase I cleavable complex. It is believed that the more persistent the cleavable complex, the more difficult it is for tumor cells to repair the DNA damage and the more cytotoxic the camptothecin. The procedure described herein can be used to prepare a number of cysteine-containing peptide derivatives of the alkylating camptothecins through the creation of stable thioether linkages.

Due to the high activity of the 7-glutathionylmethyl-derivative of 10,11-methylenedioxy-20(S)-camptothecin several additional derivatives are included in this disclosure. These derivatives are all amino acid or peptide derivatives containing a methyl cysteinyl moiety at the 7-position of 10,11-methylenedioxycamptothecin (FIG. 9). In this case, amino acid refers to any of the 20 naturally occuring amino acids or peptides. These derivatives can be prepared by procedures similar to those outlined above for GSMMDC. The sulfur of the cysteine provides the nucleophile necessary for facile displacement of the halogen of the camptothecin to form the stable thioether conjugate. The sulfhydryl-containing amino acids or sulfhydryl-containing peptides used as precursors of the conjugates of the present invention also include sulfhydryl-containing amino acids or sulfhydryl-containing peptides which have been esterified by methods well known to those or ordinary skill in the art. Compounds wherein the peptide moiety is esterified have improved cellular uptake.

The compounds of the present invention include conjugates having a 10,11-methylenedioxy-substituted CPT moiety.

The compounds of the present invention further include conjugates having a 10,11-difluoromethylenedioxy-substituted CPT moiety.

The compounds of the present invention further include conjugates which are unsubstituted at the 10,11-position of the CPT moiety.

Specific non-limiting examples of the compounds of the invention include 7-glutathionylmethyl-10,11-methylenedioxy-20(S)-CPT, 7-monoethylglutathionyl-methyl-10,11-methylenedioxy-20(S)-CPT, 7-diethylglutathhionylmethyl-10,11-methylene-dioxy-20(S)-CPT, 7-cysteinyl(thio)methyl-10,11-methylenedioxy-20(S)-CPT, 7-cysteinyl-(thio)methyl-10,11-methylenedioxy-20(S)-CPT, 7-cys-β-ala-methyl-10,11-methylenedioxy-20(S)-CPT, 7-glu-cys(thio)methyl-10,11-methylenedioxy-20(S)-CPT, 7-Glu-Cys(thio)-methyl-10,11-MD-20(S)-CPT, 7-cys-β-ala-methyl-20(S)-CPT, 7-glutathionylmethyl-20(S)-CPT, 7-monoethylglutathiomethyl-20(S)-CPT, 7-diethylglutathionylmethyl-20(S)-CPT, 7-cysteinyl(thio)methyl-20(S)-CPT and 7-cys-gly-methyl-20(S)-CPT.

The camptothecin compounds are administered in a dose which is effective to inhibit the growth of tumors. As used herein, an effective amount of the camptothecin compounds is intended to mean an amount of the compound that will inhibit the growth of tumors, that is, reduce the site of growing tumors relative to a control in which the tumor is not treated with the camptothecin-peptide conjugate. These effective amounts are generally from about 1–60 mg/kg of body weight per week, preferably about 2–20 mg/kg per week.

The conjugates of the present invention may be administered as a pharmaceutical composition containing the camptothecin-peptide conjugate and a pharmaceutically acceptable carrier or diluent. The active materials can also be mixed with other active materials which do not impair the desired action and/or supplement the desired action. The active materials according to the present invention can be administered by any route, for example, orally, parenterally, intravenously, intradermally, subcutaneously, or topically, in liquid or solid form.

For the purposes of parenteral therapeutic administration, the active ingredient may be incorporated into a solution or suspension. The solutions or suspensions may also include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. The parenteral preparation can be enclosed in ampoules, disposable syringes or multiple dose vials made of glass or plastic.

Another mode of administration of the conjugates of this invention is oral. Oral compositions will generally include an inert diluent or an edible carrier. For the purpose of oral therapeutic administration, the aforesaid conjugates may be incorporated with excipients and used in the form of tablets, gelatine capsules, troches, capsules, elixirs, suspensions, syrups, wafers, chewing gums and the like. Compositions may be prepared according to any method known to the art for the manufacture of pharmaceutical compositions and such compositions may contain one or more agents selected from the group consisting of sweetening agents, flavoring agents, coloring agents and preserving agents. Tablets containing the active ingredient in admixture with nontoxic pharmaceutically acceptable excipients which are suitable for manufacture of tablets are acceptable. These excipients may be, for example, inert diluents, such as calcium carbonate, sodium carbonate, lactose, calcium phosphate or sodium phosphate granulating and disintegrating agents, such as maize starch, or alginic acid; binding agents, such as starch, gelatin or acacia; and lubricating agents, such as magnesium stearate, stearic acid or talc. Tablets may be uncoated or may be coated by known techniques to delay disintegration and adsorption in the gastrointestinal tract and thereby provide a sustained action over a longer period. For example, a time delay material such as glyceryl monostearate or glyceryl distearate alone or with a wax may be employed. Formulations for oral use may also be presented as hard gelatin capsules wherein the active ingredient is mixed with an inert solid diluent, for example calcium caronate, calcium phosphate or kaolin, or as soft gelatin capsules wherein the active ingredient is mixed with water or an oil medium, such as peanut oil, liquid paraffin or olive oil.

The tablets, pills, capsules, troches and the like may contain the following ingredients: a binder such as microcrystalline cellulose, gum tragacanth or gelatin; an excipient such as starch or lactose, a disintegrating agent such as alginic acid, Primogel, corn starch and the like; a lubricant such as magnesium stearate or Sterotes; a glidant such as colloidal silicon dioxide; and a sweetening agent such as sucrose or saccharin or flavoring agent such as peppermint, methyl salicylate, or orange flavoring may be added. When the dosage unit form is a capsule, it may contain, in addition to material of the above type, a liquid carrier such as a fatty oil. Other dosage unit forms may contain other various materials which modify the physical form of the dosage unit, for example, as coatings. Thus tablets or pills may be coated with sugar, shellac, or other enteric coating agents. A syrup may contain, in addition to the active compounds, sucrose as a sweetening agent and certain preservatives, dyes and colorings and flavors. Materials used in preparing these various compositions should be pharmaceutically or veterinarially pure and non-toxic in the amounts used.

Aqueous suspensions of the invention contain the active materials in admixture with excipients suitable for the manufacture of aqueous suspensions. Such excipients include a suspending agent, such as sodium carboxymethylcellulose, methylcellulose, hydroxypropyl-ethyl cellulose, sodium alginate, polyvinylpyrrolidone, gum tragacanth and gum acacia, and dispersing or wetting agents such as a naturally occurring phosphatide (e.g., lecithin), a condensation product of an alkylene oxide with a fatty acid (e.g., polyoxyethylene stearate), a condensation product of ethylene oxide with a long chain aliphatic alcohol (e.g., heptadecaethylene oxycetanol), a condensation product of ethylene oxide with a partial ester derived from a fatty acid and a hexitol (e.g., polyoxyethylene sorbitol mono-oleate), or a condensation product of ethylene oxide with a partial ester derived from fatty acid and a hexitol anhydride (e.g., polyoxyethylene sorbitan mono-oleate). The aqueous suspension may also contain one or more preservatives such as ethyl or n-propyl p-hydroxybenzoate, one or more coloring agents, one or more flavoring agents and one or more sweetening agents, such as sucrose, aspartame, saccharin, or sucralose.

Oil suspensions may be formulated by suspending the active ingredient in a vegetable oil, such as arachis oil, olive oil, sesame oil or coconut oil, or in a mineral oil such as liquid paraffin. The oil suspensions may contain a thickening agent, such as beeswax, hard paraffin or cetyl alcohol. Sweetening agents may be added to provide a palatable oral preparation. These compositions may be preserved by the addition of an antioxidant such as ascorbic acid.

Dispersible powders and granules of the invention suitable for preparation of an aqueous suspension by the addition of water may be formulated from the active ingredients in admixture with a dispersing, suspending and/or wetting agent, and one or more preservatives. Suitable dispersing or wetting agents and suspending agents are exemplified by those disclosed above. Additional excipients, for example sweetening, flavoring and coloring agents, may also be present.

The pharmaceutical composition of the invention may also be in the form of oil-in-water emulsions. The oily phase may be a vegetable oil, such as olive oil or arachis oil, a mineral oil, such as liquid paraffin, or a mixture of these. Suitable emulsifying agents include naturally occurring gums, such as gum acacia and gum tragacanth, naturally occurring phosphatides, such as soybean lecithin, esters or partial esters derived from fatty acids and hexitol anhydrides, such as sorbitan mono-oleate, and condensation products of these partial esters with ethylene oxide, such as polyoxyethylene sorbitan mono-oleate. The emulsion may also contain sweetening and flavoring agents.

Syrup s and elixirs may be formulated with sweetening agents, such as glycerol, sorbitol or sucrose. Such formulations may also contain a demulcent, a preservative, a flavoring or a coloring agent.

The pharmaceutical compositions of the invention may be in the form of a sterile injectable preparation, such as a sterile injectable aqueous or oleaginous suspension. This suspension may be formulated according to the known art using those suitable dispersing or wetting agents and suspending agents which have been mentioned above. The sterile injectable preparation may also be a sterile injectable solution or suspension in a nontoxic parenterally acceptable diluent or solvent, such as a solution of 1,3-butanediol. Among the acceptable vehicles and solvents that may be employed are water and Ringer's solution, an isotonic sodium chloride. In addition, sterile fixed oils may conventionally be employed as a solvent or suspending medium. For this purpose any bland fixed oil may be employed including synthetic mono- or diglycerides. In addition, fatty acids such as oleic acid may likewise be used in the preparation of injectables. Sterilization may be performed by conventional methods known to those of ordinary skill in the art such as by aseptic filtration, irradiation or terminal sterilization (e.g. autoclaving).

Aqueous formulations (i.e oil-in-water emulsions, syrups, elixirs and injectable preparations) may be formulated to achieve the pH of optimum stability. The determination of the optimum pH may be performed by conventional methods known to those of ordinary skill in the art. Suitable buffers may also be used to maintain the pH of the formulation.

The camptothecin compounds of this invention may also be administered in the form of suppositories for rectal administration of the drug. These compositions can be prepared by mixing the drug with a suitable nonirritating excipient which is solid at ordinary temperatures but liquid at the rectal temperatures and will therefore melt in the rectum to release the drug. Non-limiting examples of such materials are cocoa butter and polyethylene glycols.

They may also be administered by intranasal, intraocular, intravaginal, and intrarectal routes including suppositories, insufflation, powders and aerosol formulations.

The camptothecin compounds of the present invention may also be administered in the form of liposome or microvesicle preparations. Liposomes are microvesicles which encapsulate a liquid within lipid or polymeric membranes. Liposomes and methods of preparing liposomes are known and are described, for example, in U.S. Pat. No. 4,452,747, U.S. Pat. No. 4,448,765, U.S. Pat. No. 4,837,028, U.S. Pat. No. 4,721,612, U.S. Pat. No. 4,594,241, U.S. Pat. No. 4,302,459 and U.S. Pat. No. 4,186,183. Suitable liposome preparations for use in the present invention are also described in WO-9318749-A1, J-02056431-A and EP-276783-A.

FIG. 4 shows the results of a topoisomerase I-DNA nicking assay. Since topoisomerase nicks DNA in a reversible reaction, a mixture of these two components results in mainly intact DNA which migrates on this gel to position 1 (visible in the control lanes x). The addition of the camptothecins (lanes x to x) inhibits religation of the DNA resulting in stabilization of the cleavable complex and nicked DNA. The nicked DNA migrates to position 2 on these gels. FIG. 4 shows that all three camptothecins tested, 10,11-methylenedioxy-20(S)-camptothecin (MDC), camptothecin (CPT) and GSMMDC induce nicked DNA. The band corresponding to nicked DNA increases as the concentration of the camptothecin is increased in each case. These data show that GSMMDC appears to induce slightly fewer nicks in the DNA as does MDC and CPT. The number of nicks in the DNA however may not be the best indicator of drug activity.

FIG. 5 shows an assay testing the stability of the cleavable complex. In this assay, nicked DNA is first formed by the action of the camptothecins. Addition of NaCl perturbs the equilibrium and destabilizes the camptothecin-topo I-DNA complex. The persistence of the nicked DNA under these conditions indicates increased stability of the cleavable complex. As indicated above, it is believed that the persistence of the cleavable complex is one of the most important determinants of the activity. The figure shows that nicked DNA of different lengths arc visible at positions A, B and C at time=0 for all of the camptothecins. However as time increases, the nicked DNA is difficult to detect after 3 minutes in camptothecin (CPT)-treated experiments. Both MDC and GSMMDC show nicked DNA for longer periods of time.

Figure 6:
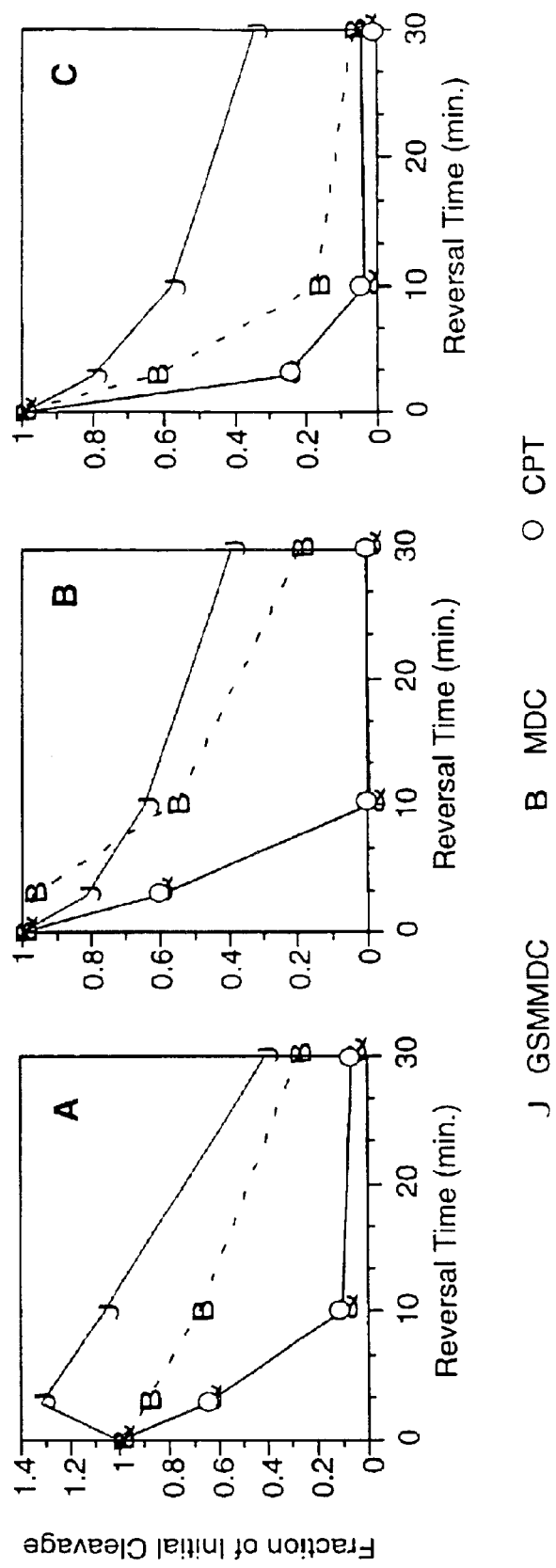
FIG. 6. Reversal kinetics of DNA cleavage produced by human topI in pSK DNA quantitation by Phopholmager.

Phosphorimager analysis of the gels shown in FIG. 5 are shown in FIG. 6. For each of the bands at position A, B, and C the results show that GSMMDC results in the slowest reversal of nicked DNA. Of all of the camptothecin analogues tested to date by this assay, the conjugate GSMMDC exhibits the slowest reversal of DNA strand breaks. This suggests that glutathione conjugates may be one of the most effective camptothecin analogues prepared.

Figure 7:
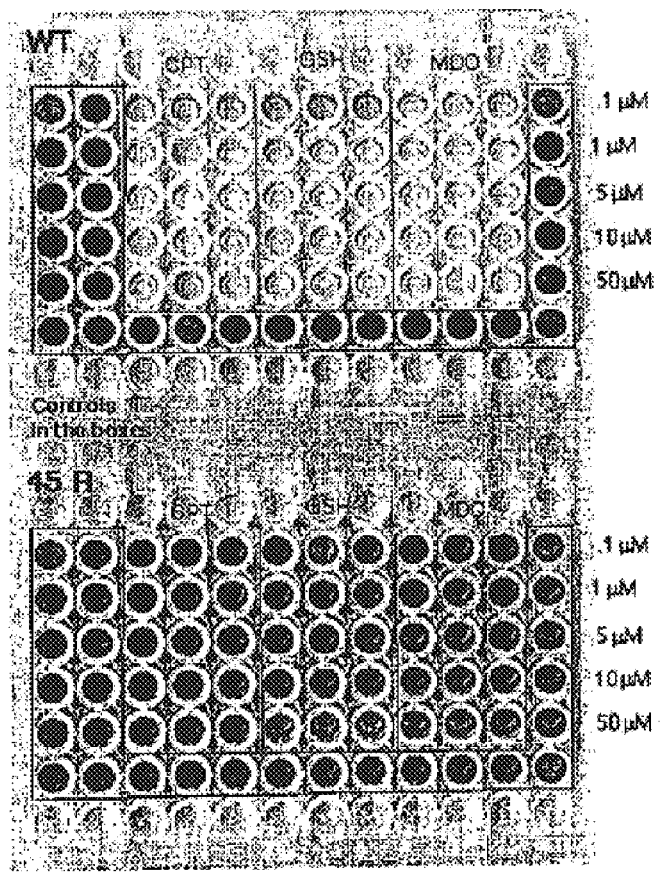
FIG. 7. MTT cytotoxicity assay on P388 WT and P388 45R cells treated with CPT derivatives.

To demonstrate that this activity is realized in the cell, the toxicity of GSMMDC was tested against human leukemia cell lines. The $IC_{50}$ for GSMMDC against the U937 leukemia cell line is 20 nM. The $IC_{50}$ for the alkylating 7-chloromethyl-10,11-methylenedioxy-20(S)-camptothecin (CMMDC) against this cell line is 7 nM. These data demonstrate that both compounds are effective anticancer agents. FIG. 7 shows a multiwell plate from an MTT cytotoxicity assay. Untreated P388 WT (wild type) cells show dark wells where cells are viable. Each of the three camptothecins, including GSMMDC, show clear wells indicating cytotoxicity down to 0.1 μM. For P388 45R cells which lack topoisomerase I, all drugs are ineffective indicating that the cytotoxicity for all, including GSMMDC, is due to topoisomerase I inhibition.

Even though the nicking assays above indicate that GSMMDC is a particularly good inhibitor of topoisomerase I, the finding that GSMMDC is at least as active in vivo against the leukemia cell lines as the other camptothecins is surprising. This is because the highly polar glutathione group attached to the 7-position of the camptothecin molecule would be expected to hinder transport of this analogue compared to the more hydrophobic CPT and MDC. More facile transport into the cell, and the realization of the enhanced toxicity of this agent, may be possible if the ionized groups of GSMMDC were blocked by ester groups (FIG. 8). This invention therefore includes the preparation of the diethyl ester of GSMMDC. This preparation is currently underway. Another derivatives would include the diisopropyl esters of GSMMDC. Both can be prepared by prior esterification of glutathione peptide followed by reaction with 7-bromomethyl- or 7-chloromethyl-10,11-methylenedioxy-20(S)-camptothecin.

The camptothecin compounds may be used individually to inhibit the growth of tumors or to treat leukemia. Alternatively, combinations of two or more camptothecin compounds may be used or combinations of one or more camptothecin compounds with one or more known anti-tumor compounds or anti-leukemic compounds. When a camptothecin-peptide conjugate is combined with a conventional anti-tumor compound, the camptothecin-peptide conjugate will generally be present in an amount ranging from about 1–99 wt. %, preferably, 5–95 wt. % of the combined amount of camptothecin-peptide conjugate and conventional anti-tumor compound. The pharmaceutical compositions noted above may contain these combinations of compounds together with an acceptable carrier or diluent.

The camptothecin compounds of the invention may be administered to treat leukemia and solid tumors in mammals, including humans. Numerous camptothecin compounds have been shown to be effective against leukemia using the standard L1210 leukemia assay (Wall et al. (1993), Journal of Medicinal Chemistry, 36:2689–2700). High activity of camptothecin and camptothecin analogs has also been shown in the P388 leukemia assay (Wall (1983), Medical and Pediatric Oncology, 11:480A–489A). The later reference also provides a correlation between anti-leukemia activity as determined by the L1210 and the P388 leukemia assays with efficacy of camptothecin compounds against solid tumors. Compounds reported as active in the leukemia assays also have demonstrated activity in a number of solid tumors including a colon xenograft, a lung xenograft, a Walker sarcoma and a breast xenograft (Wall (1983), Table IV, page 484 A). Studies have confirmed the correlation between topoisomerase I inhibitory activity and anti-leukemia/anti-tumor activity of camptothecin compounds (Giovanella et al. (1989), Science, 246: 1046–1048). The compounds of the present invention are particularly effective in the treatment of colon, lung, breast and ovary solid tumors, brain glioma and leukemia in mammals, and in particular in humans.

Other features of the invention will become apparent in the course of the following descriptions of exemplary embodiments which are given for illustration of the invention and are not intended to be limiting thereof.

EXAMPLES

Example 1

7-Hydroxymethyl-10,11-MD-20(S)-CPT

To a suspension of 10,11-MD-CPT (1.0 g, 2.55 mmol) in a mixture of MeOH (30 mL) and $H_2O$(25 mL), 75% $H_2SO_4$(25 mL) was added dropwise and then $FeSO_4 \cdot 7H_2O$ (0.8 g, 2.9 mmol) was added. To the ice cold mixture 30% $H_2O_2$(5 mL 2.2 mmol) was added dropwise in 20 min with stirring. After stirring the mixture at room temp for 16 h, it was poured onto ice/$H_2O$. The precipitate was collected and recrystallized in pyridine (0.88 g, 82% yield). $^1$H-NMR (DMSO-$d_6$) δ 0.87 (t, 3H), 1.84 (m, 2H), 5.10 (d, 2H), 5.30 (s, 2H), 5.41 (s, 2H), 5.72 (t, 1H), 6.27 (s, 2H), 6.47 (s, 1H), 7.23 (s, 1H), 7.49 (s, 2H); MS m/z 422 ($M^+$).

Example 2

7-Bromomethyl-10,11-MD-20(S)-CPT

A mixture of 7-hydroxymethyl-10,11-MD-CPT (0.5 g, 1.2 mmol), freshly distilled HBr (8 mL), and I drop of con $H_2SO_4$ was heated at 80–90° C. to 18 h. HBr was removed under reduced pressure and the residue was recrystallized in $CHCl_3$/MeOH to yield the title compound (450 mg, 78%) $^1$H-NMR(DMSO-$d_6$) δ 0.86 (t, 3H), 1.86 (m, 2H), 5.22 (s, 2H), 5.24 (s, 2H), 5.36 (s, 2H), 5.88 (s, 2H), 6.30 (s, 2H), 6.49 (s, 1H), 7.22 (s, 1H), 7.58 (s, 1H), 7.74 (s, 1H); MS m/z 486 $M^+$).

Example 3

7-Glutathionylmethyl-10,11-MD-20(S)-CPT

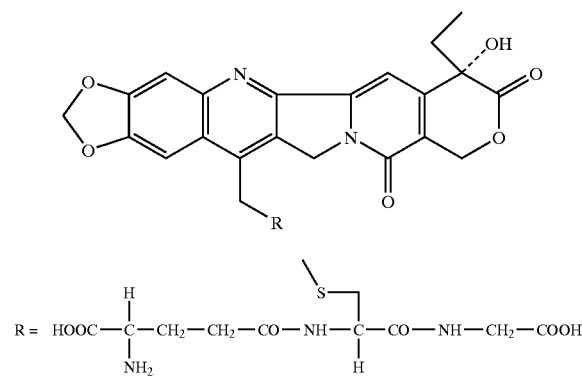

To a stirring solution of 7-bromomethyl-10,11-MD-20 (S)-CPT (115 mg, 0.24 mmol) in DMF (8 mL), a slight excess of glutathione (100 mg) in $H_2O$(1 mL) was added. After 1 h, the precipitated conjugate was collected, washed five times with water, followed by MeOH and dried to give a beige powder (148 mg, 88%) $^1$H-NMR (DMSO-$d_6$+$D_2O$) δ 0.82 (t, 3H), 1.85 (m, 2H), 2.20–3.86 (m, 9H), 4.21 (s, 2H), 4.41 (m, 1H), 5.21 (s, 2H), 5.38 (s, 2H), 6.23 (s, 2H), 7.42 (s, 1H), 7.62 (s, 1H), 7.88 (s, 1H); MS m/z 734 ($M^+$+23).

Example 4

7-Monoethylglutathionylmethyl-10,11-MD-20(S)-CPT

The title compound was prepared as described in Example 3 except that the reagent is glutathionemonoethyl ester.

Example 5

7-Diethylglutathionylmethyl-10,11-MD-20(S)-CPT

The title compound was prepared as described in Example 3 except that the reagent is glutathionediethyl ester.

Example 6

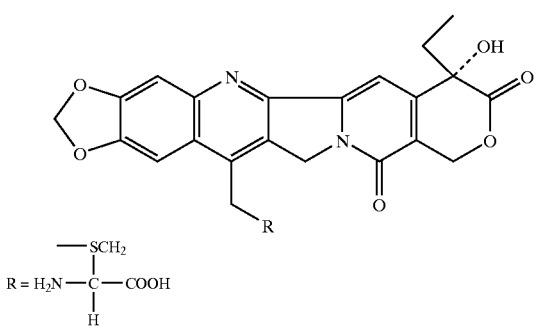

7-Cysteinyl(thio)methyl-10,11-MD-20(S)-CPT

The title compound was prepared as described in Example 3 except that the reagent used is cysteine instead of glutathione.

Example 7

7-cys-gly-methyl-10,11-MD-20(S)-CPT

The title compound was prepared as described in Example 3 except that reagent used is cysteinylglycine.

Example 8

7-cys-β-ala-methyl-10,11-MD-20(S)-CPT

The title compound was prepared as described in Example 3 except that the reagent used is cysteinyl β-alanine.

Example 9

7-Bromomethyl-20(S)-CPT

The title compound was prepared as described in Example 2 except that the starting material is 7-hydroxymethyl-20(S)-CPT.

Example 10

7-Glutathionylmethyl-20(S)-CPT

The title compound was prepared as described in Example 3 except that the starting material is 7-Bromomethyl-20(S)-CPT.

Example 11

7-Monoethylglutathiomethyl-20(S)-CPT

The title compound was prepared as described in Example 3 except that the starting material is 7-Bromomethyl-20(S)-CPT and the reagent is glutathionemonoethyl ester.

Example 12

7-Diethylglutathionylmethyl-20(S)-CPT

The title compound was prepared as described in Example 3 except that the starting material is 7-Bromomethyl-20(S)-CPT and the reagent is glutathionediethylester.

Example 13

7-Cysteinyl(thio)methyl-20(S)-CPT

The title compound was prepared as described in Example 3 except that the starting material is 7-bromomethyl-20(S)-CPT and the reagent is cysteine.

Example 14

7-Cys-Gly-Methyl-20(S)-CPT

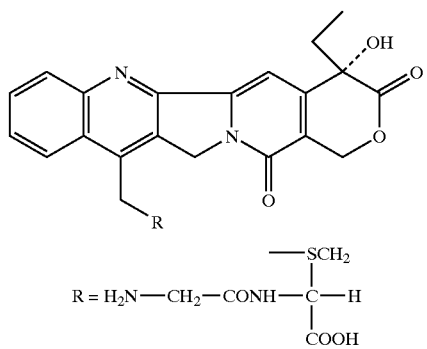

The title compound was prepared as described in Example 3 using 7-bromomethyl-20(S)-CPT and cysteinylglycine.

Example 15

7-Cys-β-ala-methyl-20(S)-CPT

The title compound was prepared as described in Example 3 using 7-bromomethyl-20(S)-CPT and cysteinyl-β-alanine.

Example 16

7-Glu-Cys(thio)methyl-10,11-MD-20(S)-CPT

The title compound was prepared as described in Example 3 except that the reagent used is glutamylcysteine instead of glutathione.

Example 17

7-Glu-Cys(thio)methyl-10,11-MD-20(S)-CPT

The title compound was prepared as described in Example 3 except that the reactants are 7-bromomethyl-CPT and Glutamylcysteine.

All the glutathio conjugates synthesized were also achieved by using 7-chloromethyl-CPT, 7-chloromethyl-10,11-MD-CPT instead of 7-bromomethyl-CPT, 7-bromomethyl-10,11-MD-CPT.

Example 18

Preparation of 7-glutathionylmethyl-10,11-methylenedioxy-20(S)-camptothecin

The conjugate 7-glutathionylmethyl-10,11-methylenedioxy-20(S)-camptothecin can be prepared in two ways:

1) To a solution of 5 mM glutathione in 0.05 M sodium phosphate pH 7.4 at 37 □C was added a 10 mM solution of the alkylating camptothecin 7-chloromethyl-10,11-methylenedioxy-20(S)-camptothecin in DMSO to a concentration of 20 μM. HPLC analysis indicated thereaction is complete in 20 minutes. The solution is filtered, applied to a solid phase extraction column and the excess glutathione is eluted by washing with dilute acetic acid. The product 7-S-glutathionylmethyl-10,11-methylenedioxy-20(S)-camptothecin (GSMMDC) is eluted from the column with 30% acetonitrile in water. The identity of the product was confirmed by mass spectrometry.

2) To a solution of 7-bromomethyl-10,11-methylenedioxy-20(S)-camptothecin (115 mg, 0.24 mmol) in slightly warm DMF (8 mL) was added a slight excess of glutathione (100 mg) in $H_2O$ (1 mL) under stirring. After 1 h, the precipitated conjugate was collected, washed five times with water and dried to give a beige powder (148 mg, 88%).

As many apparently widely different embodiments of the present invention may be made without departing from the spirit and scope thereof, it is to be construed that the present invention is not limited to the specific embodiments thereof as defined in the appended claims.

What is claimed is:

1. A compound comprising:

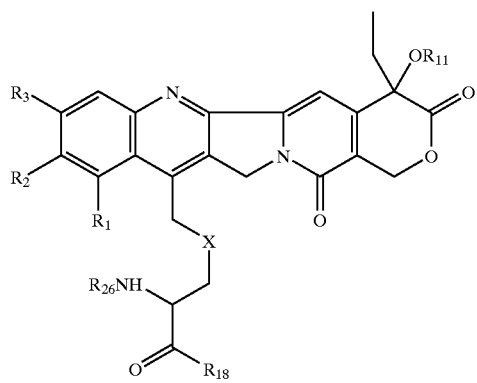

wherein $R_1$ and $R_2$, are each independently $NO_2$, $NH_2$, H, F, Cl, Br, I, COOH, OH, O—$C_{1-6}$ alkyl, SH, S—$C_{1-6}$ alkyl, CN, NH—$C_{1-6}$ alkyl, N($C_{1-6}$ alkyl)$_2$, CHO, $C_{1-8}$ alkyl, $N_3$, —Z—$(CH_2)_a$—N—$((CH_2)_bOH)_2$, wherein Z is selected from the group consisting of O, NH and S, and a and b are each independently an integer of 2 or 3, —Z—$(CH_2)_a$—N—$(C_{1-6}$ alkyl$)_2$ wherein Z is selected from the group consisting of O, NH and S, and a is an integer of 2 or 3, —$CH_2NR_4R_5$, where (a) $R_4$ and $R_5$ are, independently, hydrogen, $C_{1-6}$ alkyl, $C_{3-7}$ cycloalkyl, $C_{3-7}$ cycloalkyl-$C_{1-6}$ alkyl, $C_{2-6}$ alkenyl, hydroxy-$C_{1-6}$ alkyl, $C_{1-6}$ alkoxy-$C_{1-6}$ $COR_6$ where $R_6$ is hydrogen, $C_{1-6}$ alkyl, perhalo-$C_{1-6}$ alkyl, $C_{3-7}$ cycloalkyl, $C_{3-7}$ cycloalkyl-$C_{1-6}$ alkyl, $C_{2-6}$ alkenyl, hydroxy-$C_{1-6}$ alkyl, $C_{1-6}$ alkoxy, $C_{1-6}$ alkoxy-$C_{1-6}$ alkyl, or (b) $R_4$ and $R_5$ taken together with the nitrogen atom to which they are attached form a saturated 3–7 membered heterocyclic ring which may contain a O, S or $NR_7$ group, where $R_7$ is hydrogen, $C_{1-6}$ alkyl, perhalo-$C_{1-6}$ alkyl, aryl, aryl substituted with one or more groups selected from the group consisting of $C_{1-6}$ alkyl, halogen, nitro, amino, $C_{1-6}$ alkylamino, perhalo-$C_{1-6}$ alkyl, hydroxy-$C_{1-6}$ alkyl, $C_{1-6}$ alkoxy, $C_{1-6}$ alkoxy-$C_{1-6}$ alkyl and —$COR_8$ where $R_8$ is hydrogen, $C_{1-6}$ alkyl perhalo-$C_{1-6}$ alkyl, $C_{1-6}$ alkoxy, aryl, and aryl substituted with one or more $C_{1-6}$ alkyl, perhalo-$C_{1-6}$ alkyl, hydroxy-$C_{1-6}$ alkyl, or $C_{1-6}$ alkoxy-$C_{1-6}$ alkyl groups;

$R_3$ is H; or or $R_2$ and $R_3$ combine to form a ring

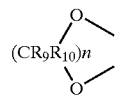

where $R_9$ and $R_{10}$ are each independently H or F and n is an integer of 1 or 2;

$R_{11}$ is H, or $C(O)$—$(CH_2)_m NR_{12}R_{13}$, where m is an integer of 1–6 or —$C(O)CHR_{14}NR_{12}R_{13}$, where $R_{14}$ is the side chain of one of the naturally occurring -amino acids, $R_{12}$ and $R_{13}$ are, independently, hydrogen, $C_{1-8}$ alkyl or —$C(O)CHR_{15}NR_{16}R_{17}$, where $R_{15}$ is the side chain of one of the naturally occurring -amino acids and $R_{16}$ and $R_{17}$ are each independently hydrogen or $C_{1-8}$ alkyl;

$R_{18}$ is $OR_{19}$ or $R_{19}OC(O)$—$(CH_2)_m$—$NR_{20}$, or $R_{21}OC(O)CHR_{22}NR_{20}$, where $R_{19}$ is H or $C_{1-6}$ alkyl, m is an integer of 1–6, $R_{22}$ is the side chain of one of the naturally occurring -amino acids, $R_{20}$ is hydrogen, $C_{1-8}$ alkyl or —$C(O)CHR_{23}NR_{24}R_{25}$, where $R_{23}$ is the side chain of one of the naturally occurring -amino acids and $R_{24}$ and $R_{25}$ are each independently hydrogen or $C_{1-8}$ alkyl;

$R_{26}$ is H or

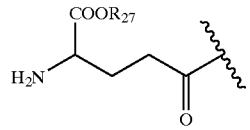

where $R_{27}$ is H or $C_{1-6}$ alkyl; and

X is S or O, or a pharmaceutically acceptable salt thereof.

2. The compound of claim 1, which is selected from the group consisting of 7-glutathionylmethyl-10,11-methylenedioxy-20(S)-CPT, 7-monoethylglutathionylmethyl-10,11-methylenedioxy-20(S)-CPT, 7-diethylglutathionylmethyl-10,11-methylenedioxy-20(S)-CPT, 7-cysteinyl(thio)methyl-10,11-methylenedioxy-20(S)-CPT, 7-cysteinyl(thio)methyl-10,11-methylenedioxy-20(S)-CPT, 7-cys-ala-methyl-10,11-methylenedioxy-20(S)-CPT, 7-glu-cys(thio)methyl-10,11-methylenedioxy-20(S)-CPT, 7-Glu-Cys(thio)methyl-10,11-MD-20(S)-CPT, 7-cys-ala-methyl-20(S)-CPT, 7-glutathionylmethyl-20(S)-CPT, 7-monoethylglutathiomethyl-20(S)-CPT, 7-diethylglutathionylmethyl-20(S)-CPT, 7-cysteinyl(thio)methyl-20(S)-CPT and 7-cys-gly-methyl-20(S)-CPT.

3. The compound of claim 1 wherein $R_{27}$ is $C_{1-6}$ alkyl.

4. A pharmaceutical composition comprising an effective amount to treat leukemia of a compound claim 1 and a pharmaceutically acceptable carrier.

5. A method of treating leukemia in a mammal in need thereof, comprising administering to the mammal an effective amount for treating leukemia of the compound of claim 1.

6. The method of claim 5, wherein the mammal is a human.

7. A method for inhibiting the enzyme topoisomerase I, comprising contacting a DNA-topoisomerase I complex with the compound of claim 1.

8. A method for stabilizing the topoisomerase I-DNA cleavable complex, comprising contacting a DNA-topoisomerase I cleavable complex with the compound of claim 1.

* * * * *

UNITED STATES PATENT AND TRADEMARK OFFICE
CERTIFICATE OF CORRECTION

PATENT NO. : 6,825,206 B1
DATED : November 30, 2004
INVENTOR(S) : Michael P. Gamcsik et al.

It is certified that error appears in the above-identified patent and that said Letters Patent is hereby corrected as shown below:

Column 4,
Line 38, add new line as follows: -- provided that $R_{18}$ and $R_{26}$ are not both H; --

Column 6,
Line 62, add new line as follows: -- provided that $R_{18}$ and $R_{26}$ are not both H; --

Column 9,
Lines 7 and 8, delete "difluromethylenedioxy groups" and insert -- difluoromethylenedioxy groups --

Column 10,
Line 20, delete "Where, $R_{18}$ s $OR_{19}$..." and insert -- Where $R_{18}$ is $OR_{19}$ --
Line 37, add new line as follows: -- provided that $R_{18}$ and $R_{19}$ are not both H. --

Column 12,
Line 28, delete "caronate" and insert -- carbonate --

Column 16,
Line 15, delete "(s,IH)" and insert -- (s,1H) --
Line 24, delete "and I drop" and insert -- and 1 drop --

Signed and Sealed this

Twenty-fourth Day of May, 2005

JON W. DUDAS
*Director of the United States Patent and Trademark Office*